(12) United States Patent
Widmann

(10) Patent No.: US 7,052,505 B2
(45) Date of Patent: May 30, 2006

(54) SURGICAL INSTRUMENT

(76) Inventor: Heinrich Widmann, Almenweg 18, 88637, Buchheim (DE)

( * ) Notice: Subject to any disclaimer, the term of this patent is extended or adjusted under 35 U.S.C. 154(b) by 171 days.

(21) Appl. No.: 10/469,569

(22) PCT Filed: Feb. 27, 2002

(86) PCT No.: PCT/EP02/02107

§ 371 (c)(1),
(2), (4) Date: Aug. 28, 2003

(87) PCT Pub. No.: WO02/069815

PCT Pub. Date: Sep. 12, 2002

(65) Prior Publication Data

US 2004/0073232 A1 Apr. 15, 2004

(30) Foreign Application Priority Data

Mar. 1, 2001 (DE) .......................... 201 03 630 U

(51) Int. Cl.
*A61B 17/32* (2006.01)

(52) U.S. Cl. ...................................... 606/167; 606/170
(58) Field of Classification Search ........ 606/205–211, 606/167, 168, 169, 170
See application file for complete search history.

(56) References Cited

FOREIGN PATENT DOCUMENTS

DE         004316769 C1 *  5/1994
WO         WO 95/05123   *  2/1995

* cited by examiner

*Primary Examiner*—Anhtuan T. Nguyen
*Assistant Examiner*—Charles Sam
(74) *Attorney, Agent, or Firm*—Bachman & LaPointe, P.C.

(57) ABSTRACT

A surgical instrument comprising a linear element (1) and an insert or catch (7) that is slidably and releasably arranged in or on the linear element (1). The insert or catch (7) or a guide element (8.1, 8.2) associated therewith is guided relative to the linear element (1) on at least one guide track (11.1, 11.2; 12.1, 12.2). The instrument is further characterized in that a stop (14) can be displaced behind the insert or catch (7) or the guide element (8.2) in or out from the guide track (11.2; 12.2).

12 Claims, 2 Drawing Sheets

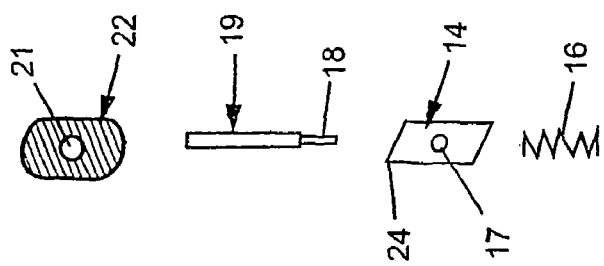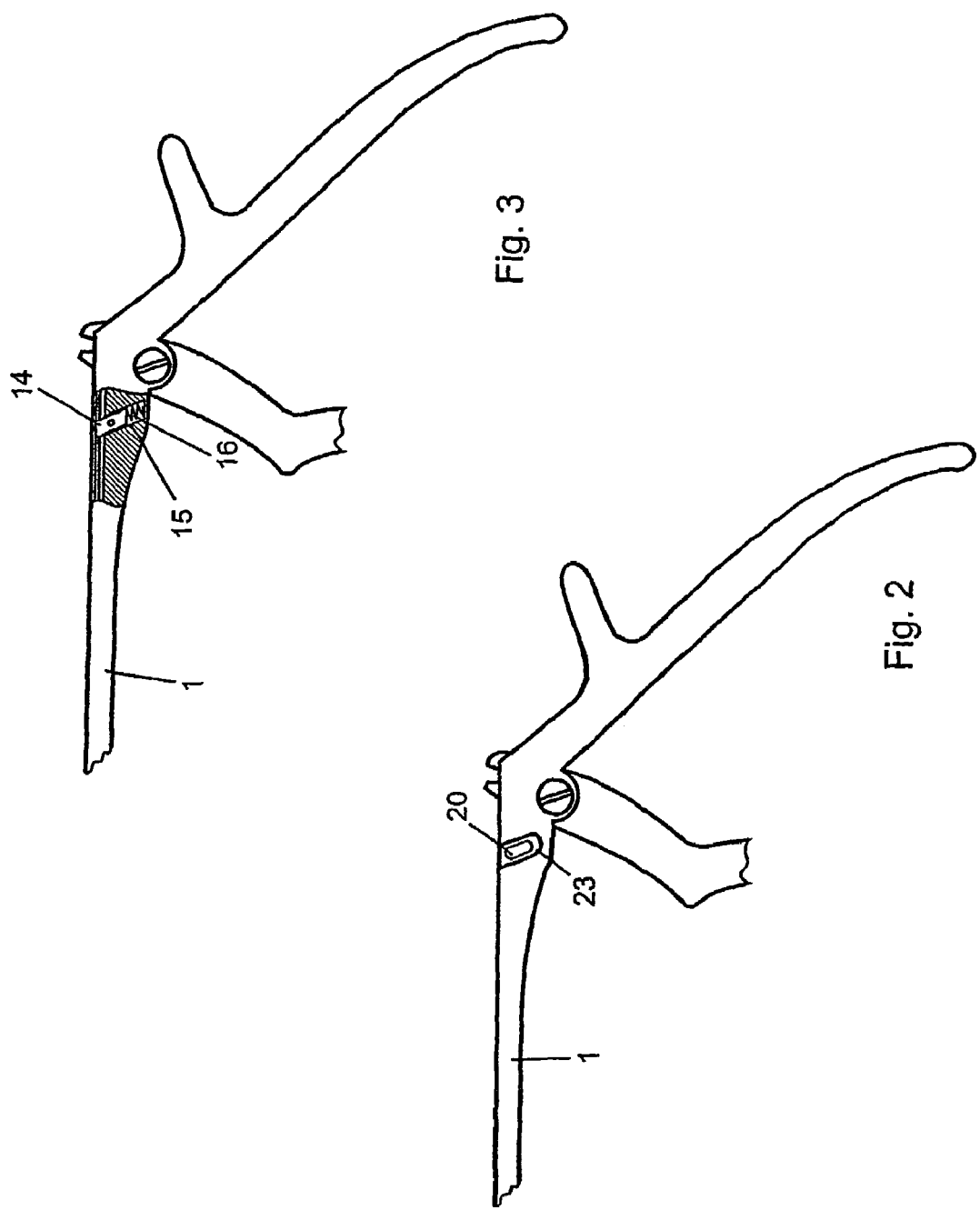

SURGICAL INSTRUMENT

BACKGROUND OF THE INVENTION

The invention relates to a surgical instrument with a linear element and with an insert or attachment which is arranged slidably and releasably in or on the linear element, the insert or attachment, and a guide element assigned thereto, being guided relative to the linear element on at least one guide track, and a stop being movable behind the insert or attachment or the guide element into or out from the guide track.

The present invention is intended to relate to all possible types of surgical instruments, for example including tubular shaft instruments. However, it relates in particular to sliding shaft instruments. These are used to carry out cutting, shearing, clamping or similar operations, for example in the human body. In these operations, suitable handpieces are used to move the slide along a slide surface of the shaft, and a jaw is generally actuated at the end thereof.

Sliding shaft instruments of this kind are used in particular as bone punches, as ear forceps, and in gynecological biopsies. A general problem is that surgical instruments of this kind are products which have a very wide variety of hinges, guides or grooves and channels. Such instruments are therefore extremely difficult to clean and sterilize, but cleaning of surgical instruments is of course of the utmost importance. The hygiene requirements for such surgical instruments are greatly increased due to the risk of transmission of diseases, for example hepatitis or AIDS.

A sliding shaft instrument is known from DE 43 16 769 C1, for example. In this instrument, however, there is a danger of the slide inadvertently coming loose from the shaft.

EP 0 838 198 A discloses a surgical instrument in which a push/pull rod is guided in an outer tube in order to move jaw parts. This rod has two recesses, a screw engaging in one recess, and a locking lug of a forceps arm engaging in the other recess. To release the rod, the screw must be loosened by hand.

DE 197 13 067 A discloses an arthroscopy instrument in which a push/pull rod is likewise guided in an outer tube. This rod has a depression in the area of the handpiece. To secure the rod in the handpiece and to release the rod, use is made of a threaded pin with a half recess. For releasing or securing, the threaded pin has to be turned through 180°.

A surgical instrument of the abovementioned type is known from WO 95/05123. In this, a pin protruding from a slide is guided in a slit of a sliding shaft element. A press button engages in this slit, which press button can be moved counter to the force of a spring. In the slit, the press button has a stop which limits the movement of the pin and thus of the slide. By pressing on the press button, this stop is moved out from the clear width of the slit so that the slide can be moved farther toward the rear, with the result that a T-shaped rail disengages from a correspondingly shaped groove of the shaft element and the slide can be removed from the shaft element. When assembling the instrument, the press button again has to be activated so that the pin comes to a position behind the stop.

The object of the present invention is to develop an instrument of the above mentioned type in which inadvertent release of the insert or attachment from the linear element is effectively avoided, but which at the same time permits easy dismantling and assembly.

SUMMARY OF THE INVENTION

The foregoing object is achieved by providing a stop which is guided obliquely at an obtuse angle, preferably from below, to the guide track.

In the case of a sliding shaft instrument for example, this design ensures that the slide and its guide elements do not inadvertently slide out from a longitudinal groove, resulting in the slide inadvertently being separated from the shaft.

The stop is preferably guided in a blind hole in the shaft and engages from below into the clear width of the guide track or into a longitudinal groove. The blind hole is set at an inclination with respect to the groove, so that the stop designed as pressure pin also supports the guide element obliquely from behind. This improves the support of the guide element.

In the blind hole itself, the pressure pin in turn bears against an energy-accumulating means, preferably against a helical spring. This means that the pressure pin is held in the locked position, unless its position is deliberately altered. Only when the pressure pin is deliberately moved counter to the force of the helical spring can the pressure pin be guided out from the locked position, for which purpose a slide button is provided on the outside of the shaft. The slide button is connected via a connection pin to the pressure pin, and, for easier assembly, the pressure pin is screwed with a threaded shaft into a threaded bore in the pressure pin. The slide button itself is guided in a channel on the outside of the shaft.

BRIEF DESCRIPTION OF THE DRAWINGS

Further advantages, features and details of the invention will become evident from the following description of preferred illustrative embodiments and with reference to the drawing, in which:

FIG. 2 shows a plan view of parts of the sliding shaft instrument according to FIG. 1;

FIG. 3 shows a plan view of parts of the sliding shaft instrument according to FIG. 1, partially in section;

FIG. 4 shows plan views of parts of a locking mechanism for the sliding shaft instrument according to FIG. 1.

DETAILED DESCRIPTION

Figure 1:
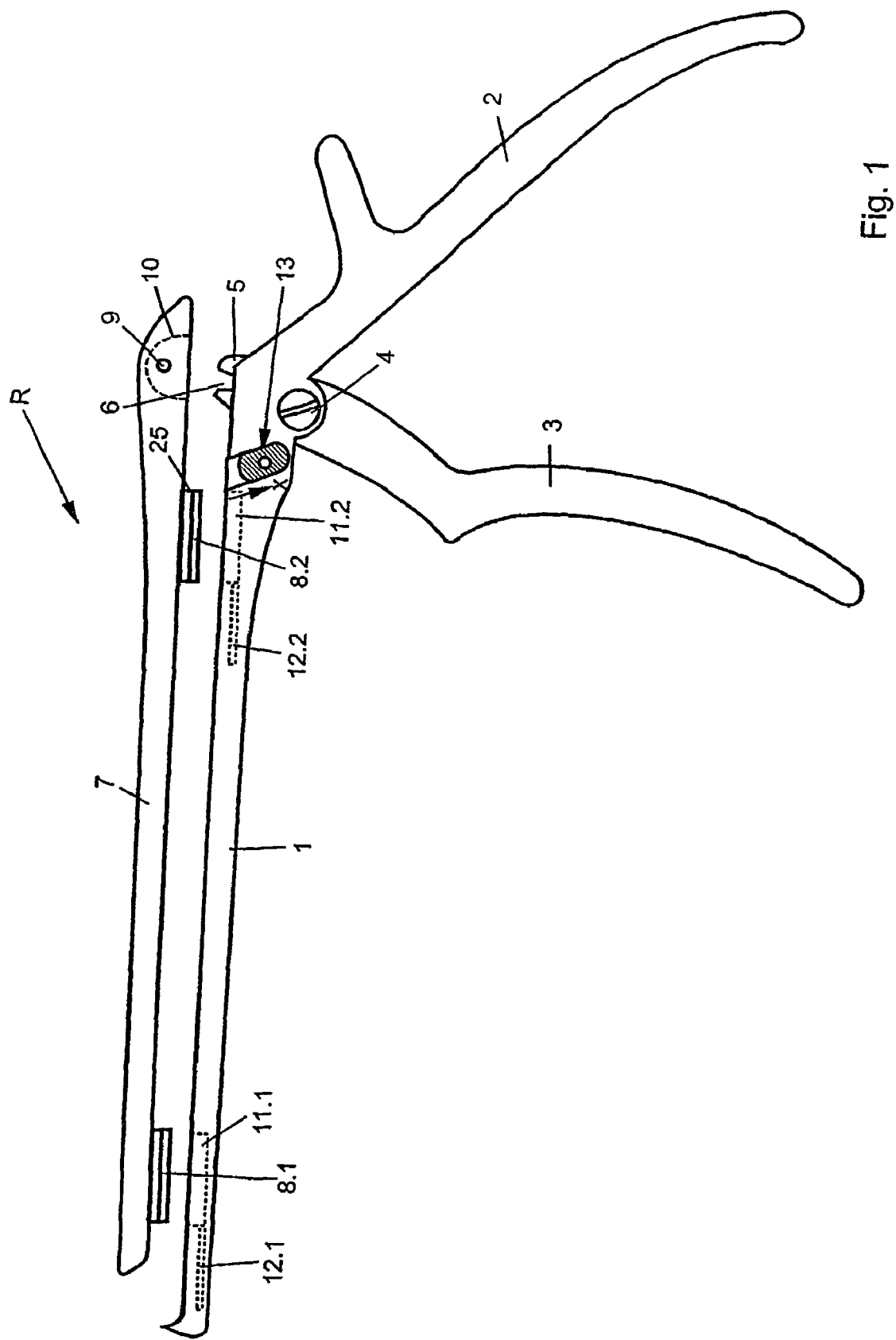
FIG. 1 shows a plan view of a sliding shaft instrument according to the invention.

According to FIG. 1, a sliding shaft instrument R has a shaft 1 which merges integrally into a handpiece 2. Fitted between the shaft 1 and the handpiece 2 there is a further handpiece 3 which is connected to the shaft 1 in an articulated manner via a screw 4. The handpiece 3 extends through the shaft 1 and at the other side protrudes from the shaft 1 via an end 5, a slit 6 being formed in the end 5.

The shaft 1 is assigned a slide 7 which has two guide elements 8.1 and 8.2. At one end, the slide 7 also has a transverse pin 9 which extends through a recess 10 (indicated by broken lines). When the sliding shaft instrument is being assembled, this recess 10 serves to receive the end 5 of the handpiece 3, the transverse pin 9 sliding into the slit 6. At the same time the guide elements 8.1 and 8.2 also engage in grooves 11.1 and 11.2 in the shaft 1 and can then be guided in longitudinal grooves 12.1 and 12.2.

According to the invention, at least the groove 11.2 behind the guide element 8.2 is assigned a locking mecha nism 13. According to FIG. 4, this locking mechanism 13 consists of four parts. The actual locking is effected by a pressure pin 14 which, in the use position according to FIG. 3, slides in a blind hole 15 formed in the shaft 1. In the blind hole 15, the pressure pin 14 bears against a spring 16. The spring 16 seeks to push the pressure pin 14 out of the blind hole 15 so that the pressure pin 14 engages in the clear width of the groove 11.2.

The pressure pin 14 also has a threaded bore 17 into which a threaded portion 18 of a connection pin 19 can be fitted. In the position of use, this connection pin 19 extends through an oblong hole 20 in the shaft 1 (see FIG. 2).

After passing through the oblong hole 20, the connection pin 19 engages in a bore 21 of a slide button 22 and is connected to this slide button 22. The slide button 22 is guided in a channel 23 in the shaft 1, said channel 23 being formed in the shaft 1 from the outside direction.

The mode of functioning of the present invention is as follows:

On assembling the surgical instrument R according to the invention, the slide 7 is placed on the shaft 1, the transverse pin 9 sliding into the slit 6. The guide element 8.1 engages in the groove 11.1 and the guide element 8.2 engages in the groove 11.2, the pressure pin 14 being forced into the blind hole 15 counter to the force of the spring 16. As soon as the guide element 8.2 has reached the bottom of the groove 11.2, the pressure pin 14 snaps behind the guide element 8.2 when a control edge 24, on account of the inclined position of the blind hole 15, has reached the rear edge 25 of the guide element 8.2. At this point, the guide element 8.2 has already slid to a slight extent into the longitudinal groove 12.2, so that the T-shaped guide element 8.2 is caught in the longitudinal groove 12.2. The longitudinal groove 12.2 is also T-shaped in cross section and thus represents an undercut groove for the guide element 8.2.

The instrument can now be used and the slide 7 cannot come loose from the shaft.

However, in order to release the slide 7 from the shaft 1, the slide button 22 is moved in direction x, by which means the pressure pin 14 can be lowered into the blind hole 15 counter to the force of the spring 16. In this way, the clear width of the groove 11.2 is again freed, so that the guide element 8.2 can slide out of the longitudinal groove 12.2 and can be removed from the groove 11.2. At this point, the guide element 8.1 can also be removed from the groove 11.1 and the transverse pin 9 from the slit 6.

The invention claimed is:

1. A surgical instrument comprising a linear element (1) and guide means (7, 8.1, 8.2) associated therewith for guided movement relative to the linear element (1) on at least one guide track (11.1, 11.2; 12.1, 12.2), wherein a movable stop (14) is located behind the guide means and is movable into or out of the guide track (11.2, 12.2), wherein the stop (14) is guided at an inclination to the guide track (11.2).

2. The surgical instrument as claimed in claim 1, wherein the guide means comprises an attachment element (7) and a guide element (8.1, 8.2).

3. The surgical instrument as claimed in claim 1, wherein the stop (14) has a control edge (24) which, in a locked position, holds the guide element (8.1, 8.2) on the guide track (11.1, 11.2; 12.1, 12.2) and, in an unlocked position, permits a greater displacement path of the attachment element (7) relative to the linear element (1), so that the guide element (8.1, 8.2) is released from the guide track (11.1, 11.2; 12.1, 12.2).

4. The surgical instrument as claimed in claim 1, wherein the stop (14) is guided in a blind hole (15) in the linear element (1).

5. The surgical instrument as claimed in claim 1, wherein the stop (14) bears against an energy-accumulating means (16).

6. The surgical instrument as claimed in claim 5, wherein the energy-accumulating means is a helical spring (16).

7. The surgical instrument as claimed in claim 1, wherein the stop (14) is connected via a connection pin (19) to a slide button (22) located on the outside of the linear element (1).

8. The surgical instrument as claimed in claim 7, wherein the connection pin (19) has a threaded portion (18) with which it can be fitted into a threaded bore (17) in the stop.

9. The surgical instrument as claimed in claim 7, wherein the slide button (22) is guided in a channel (23) in the linear element (1).

10. The surgical instrument as claimed in claim 2, wherein the linear element comprises a shaft (1) and the attachment element is a slide (7) of a sliding shaft instrument, said shaft (1) having a longitudinal groove (11.1, 11.2; 12.1, 12.2) as guide.

11. The surgical instrument as claimed in claim 1, wherein a pressure pin (14) is provided as stop.

12. The surgical instrument as claimed in claim 1, wherein the moveable step is movable obliquely at an obtuse angle with respect to the guide track.

* * * * *